United States Patent [19]

De Visser

[11] Patent Number: 5,733,240
[45] Date of Patent: Mar. 31, 1998

[54] DEVICE FOR ADMINISTERING SOUND WAVES AND/OR A MAGNETIC FIELD TO A PATIENT

[76] Inventor: Lena De Visser, Toverfluitstraat 23, NL-3194 VS Hoogvliet, Netherlands

[21] Appl. No.: 557,048
[22] PCT Filed: Jun. 1, 1994
[86] PCT No.: PCT/NL94/00125
  § 371 Date: May 6, 1996
  § 102(e) Date: May 6, 1996
[87] PCT Pub. No.: WO94/27675
  PCT Pub. Date: Dec. 8, 1994

[30] Foreign Application Priority Data

Jun. 1, 1993 [NL] Netherlands ............... 9300938

[51] Int. Cl.$^6$ ............... A61N 2/00
[52] U.S. Cl. ............... 600/9; 600/26
[58] Field of Search ............... 600/9, 26–28; 128/897–98

[56] References Cited

FOREIGN PATENT DOCUMENTS

| | | |
|---|---|---|
| 732425 | 10/1969 | Belgium . |
| 0422253 | 4/1991 | European Pat. Off. . |
| 3911679 | 10/1990 | Germany . |
| 7207379 | 12/1972 | Netherlands . |

*Primary Examiner*—John P. Lacyk
*Attorney, Agent, or Firm*—Webb Ziesenheim Bruening Logsdon Orkin & Hanson, P.C.

[57] ABSTRACT

The invention relates to a device for administering sound waves and/or at least one magnetic field to a patient, including a housing in which are accommodated a source for generating low-frequency sound waves, at least one source for generating a magnetic field and means for adjusting the frequency of the sound waves. The source for generating the sound waves is preferably formed by a speaker and the source for generating a magnetic field by a coil. The housing includes for instance a tube open on one side for passage of the sound waves and/or the magnetic field, wherein the means for concentrating the sound waves and/or the magnetic field are formed by a cover of the open side of the tube, in which the cover is provided with an aperture.

18 Claims, 1 Drawing Sheet

DEVICE FOR ADMINISTERING SOUND WAVES AND/OR A MAGNETIC FIELD TO A PATIENT

BACKGROUND OF THE INVENTION

The invention relates to a device for administering sound waves and/or a magnetic field to a patient.

Diverse such devices have already been described. These combine only a permanent magnetic field with ultrasonics.

SUMMARY OF THE INVENTION

It has now been found however that with low-frequency sound waves better results are obtained in treating poor blood circulation and/or in relieving pain. It is known that magnetic fields have a beneficial effect on bones, joints and muscles. The present invention provides a device with produces the positive results of administering the sound waves, optionally in combination with the therapeutic effect of a magnetic field. This is achieved by a device including a housing in which is accommodated a source for generating low-frequency sound waves, at least one source for generating a magnetic field and means for adjusting the frequency of the sound waves.

The source for generating the sound waves is preferably formed by a speaker. The dimensions of the speaker, in addition to the frequency generated thereby, can be varied depending on the situation. In preference sound waves of a frequency between 10 and 180 Hertz are applied. The most used frequency varies however between 145 and 155 Hertz. The sound wave is preferably a sinus wave which is generated via a memory element.

In a preferred embodiment of the invention the frequency of the wave varies within a range of a number of Hertz above and below the central frequency. The frequency preferably fluctuates between 5 Hertz above the central frequency and 5 Hertz below the central frequency. This is particularly advantageous because it has been found that use of a fixed, non-varying frequency results in habituation of a patient. Variation in the frequency can prevent this habituation.

The frequency of the magnetic field preferably lies between 1 and 25 Hertz at a field strength of 1 to 15 mT in the middle of the coil. The associated coil preferably has 200 turns of 1 mm$^2$.

Optimum operation of the device is achieved when both the sound waves and the magnetic field are administered no the body in a controlled manner. This can be achieved by propagating the sound waves and the magnetic field through a small aperture in the housing of the device. No sound waves and/or magnetic field is hereby lost.

The device according to the invention can take diverse forms of appearance. It is first of all possible to accommodate the sound source in a tubular housing which is easy to handle and can be placed on any desired location of the body for treating. In such a device the coil is arranged at the outlet for the sound waves. Preferably situated over the coil is a rubber ring for concentrating both the magnetic field and the sound waves. The housing is preferably embodied in 3 mm-thick aluminium. This is important with respect to the sturdiness of the housing, since the housing itself may not vibrate along with the sound waves.

In another embodiment the device includes a box in which the speaker is arranged. This box is again provided with a reduced-size aperture for passage of the sound waves and/or the magnetic field. In a particular embodiment of the invention two apertures are arranged for passage of the sound waves and/or the magnetic field which preferably have the form of a human foot. The applying of the sound waves and/or the magnetic field to the feet of the patient has the advantage that in this manner the whole body can be reached by means of the sound waves.

The device according to the invention can likewise be used under water. The patient is in this case placed for instance in a bath while sound waves and/or a magnetic field are likewise administered to him under water using the device. Administering can take place on the feet but also on any other desired location on the body.

BRIEF DESCRIPTION OF THE DRAWINGS

The present invention will be further elucidated with reference to the annexed drawings, in which.

DESCRIPTION OF THE PREFERRED EMBODIMENTS

Figure 1:
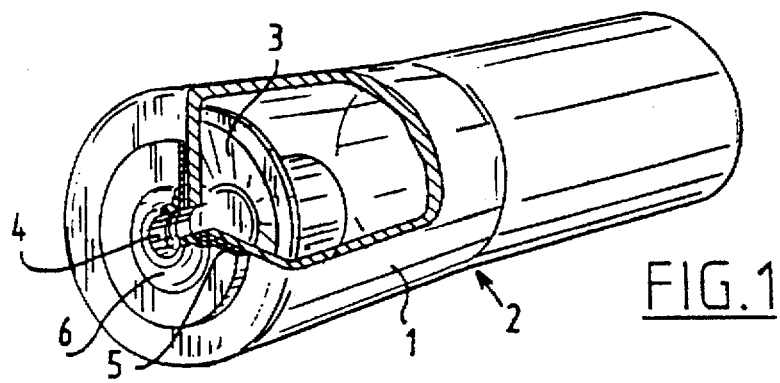
FIG. 1 shows a partly broken away perspective view of a tubular device according to the invention which can be held in the hand.

FIG. 1 shows a tubular housing 1 which is provided in this case with a constriction 2 whereby manipulation of the device is facilitated. Received in the housing is a speaker 3 for generating sound waves which leave the housing via an aperture 4. Arranged round aperture 4 is a coil 5 for generating, if desired, a magnetic field. Over the coil is situated a ring 6, for instance made of rubber, for concentrating the sound waves as well as the magnetic field.

Figure 2:
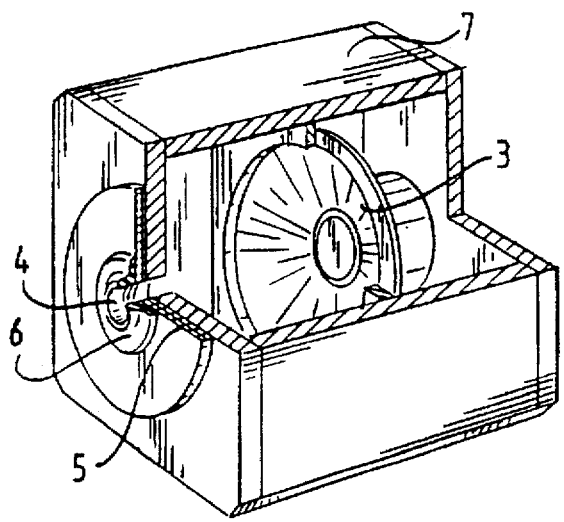
FIG. 2 shows a partly broken away perspective view of a larger non-portable embodiment of the present invention.

FIG. 2 shows another embodiment of the invention in which at a distance from the aperture 4 a speaker 3 is arranged in a housing 7, made for example of wood. The wooden housing also serves as acoustic box. Similarly to FIG. 1 the coil 5, which is covered by means of rubber ring 6, is situated here round aperture 4.

Figure 3:
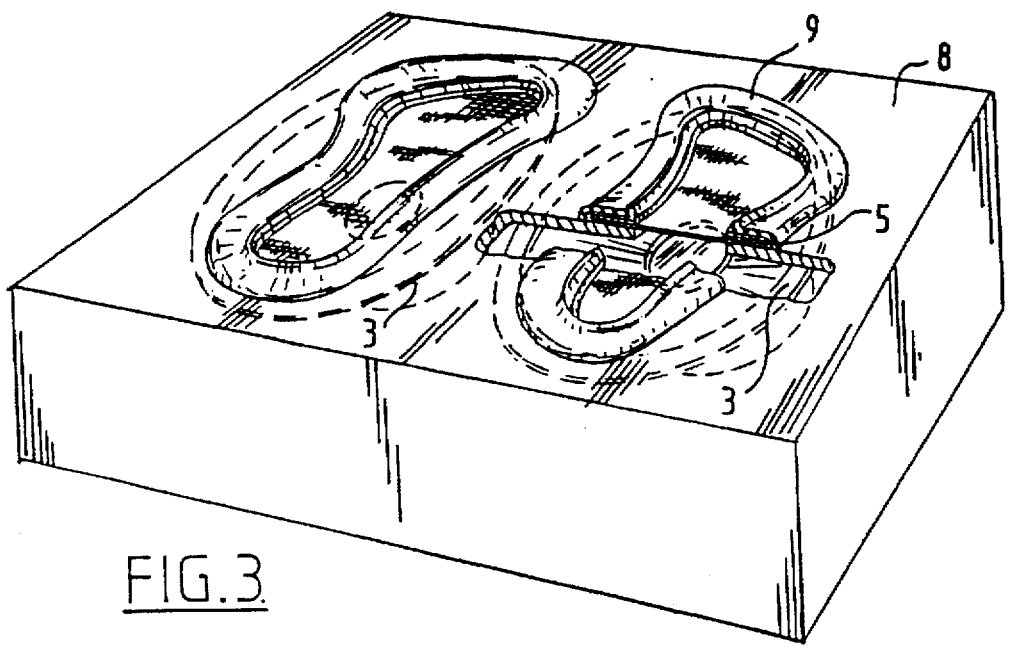
FIG. 3 is a partly broken away perspective view of a third embodiment of the device according to the invention.

The most comprehensive embodiment is shown in FIG. 3. Two speakers 3 are arranged in a housing 8. It is also possible to use only one large speaker. The rubber rings in this case have recesses in the form of a foot. A coil 5 is also arranged under the rubber rings 9.

By means of the present invention it becomes possible to administer low-frequency sound waves and a magnetic field to a patient simultaneously or independently of each other. The frequency of the sound waves and the magnetic field and the duration of the treatment are both adjustable. In preference however, only a number of possible combinations of frequency and treatment duration are possible in portable embodiments of the invention in order to prevent the patient being subjected to an irresponsibly large dose of sound waves and/or magnetic field.

I claim:

1. A device for administering at least one of sound waves and a magnetic field to a patient, comprising a housing in which are accommodated a source for generating low-frequency sound waves, at least one source for generating a magnetic field, in which said at least one source for generating said magnetic field is separate from the source for generating sound waves, and a means for adjusting the frequency of the sound waves, wherein said housing includes an aperture for passage of the sound waves and the magnetic field therethrough.

2. The device as claimed in claim 1, wherein said source for generating the sound waves is formed by a speaker.

3. The device as claimed in claim 1, wherein said at least one source for generating a magnetic field is formed by a coil.

4. The device as claimed in claim 1, further including a means for concentrating the sound waves.

5. The device as claimed in claim 1, wherein said housing includes a tube opening on one side for passage of the sound waves and the magnetic field, and wherein the means for concentrating the sound waves and the magnetic field are formed by a cover for said tube opening, in which said cover is provided with an aperture.

6. The device as claimed in claim 1, wherein said housing is formed by a box, on one side of which at least one recess is adapted for passage of the sound waves and the magnetic field and for placing therein at least one foot of the patient.

7. The device as claimed in claim 2, wherein said source for generating a magnetic field is formed by a coil.

8. The device as claimed in claim 2, further including a means for concentrating the sound waves.

9. The device as claimed in claim 2, wherein said housing includes a tube opening on one side for passage of the sound waves and the magnetic field, and wherein the means for concentrating the sound waves and the magnetic field are formed by a cover for said tube opening, in which said cover is provided with an aperture.

10. The device as claimed in claim 3, wherein said housing includes a tube opening on one side for passage of the sound waves and the magnetic field, and wherein the means for concentrating the sound waves and the magnetic field are formed by a cover for said tube opening, in which said cover is provided with an aperture.

11. The device as claimed in claim 4, wherein said housing includes a tube opening on one side for passage of the sound waves and the magnetic field, and wherein the means for concentrating the sound waves and the magnetic field are formed by a cover for said tube opening, in which said cover is provided with an aperture.

12. The device as claimed in claim 2, wherein said housing is formed by a box, on one side of which at least one recess is adapted for passage of the sound waves and the magnetic field and for placing therein at least one foot of the patient.

13. The device as claimed in claim 3, wherein said housing is formed by a box, on one side of which at least one recess is adapted for passage of the sound waves and the magnetic field and for placing therein at least one foot of the patient.

14. The device as claimed in claim 4, wherein said housing is formed by a box, on one side of which at least one recess is adapted for passage of the sound waves and the magnetic field and for placing therein at least one foot of the patient.

15. A device for administering at least sound waves and at least one magnetic field to a patient comprising a housing, a source in said housing for generating low-frequency sound waves, at least one source in said housing for generating a magnetic field and means for adjusting the sound waves frequency, wherein said housing is formed by a box, on one side of which at least one recess is adapted for passage of the sound waves and the magnetic field and for placing therein at least one foot of the patient.

16. The device as claimed in claim 15, wherein said source for generating the sound waves is formed by a speaker.

17. The device as claimed in claim 15, wherein said at least one source for generating a magnetic field is formed by a coil.

18. The device as claimed in claim 15, further including a means for concentrating the sound waves.

* * * * *